United States Patent [19]

Kim et al.

[11] Patent Number: 5,896,432
[45] Date of Patent: Apr. 20, 1999

[54] BRAZELESS ELECTROCHEMICAL CORROSION POTENTIAL SENSOR

[75] Inventors: Young Jin Kim, Clifton Park, N.Y.; Samson Hettiarachchi, Menlo Park, Calif.; Minyoung Lee, Schenectady; Svante Prochazka, Ballston Lake, both of N.Y.

[73] Assignee: General Electric Company, Schenectady, N.Y.

[21] Appl. No.: 08/928,123

[22] Filed: Sep. 12, 1997

[51] Int. Cl.⁶ .............................. G21C 9/00; G01N 27/30
[52] U.S. Cl. .................... 376/305; 376/249; 376/256; 204/400; 204/435; 324/446
[58] Field of Search .............................. 376/245, 249, 376/256, 305; 204/400, 435; 205/775.5, 794.5; 324/446, 449

[56] References Cited

U.S. PATENT DOCUMENTS

| | | | |
|---|---|---|---|
| 4,978,921 | 12/1990 | Indig et al. | 324/446 |
| 4,990,855 | 2/1991 | Niedrach et al. | 324/449 |
| 5,043,053 | 8/1991 | Indig et al. | 204/421 |
| 5,118,913 | 6/1992 | Taylor | 204/435 |
| 5,192,414 | 3/1993 | Indig et al. | 204/400 |
| 5,203,984 | 4/1993 | Sakai et al. | 204/435 |
| 5,217,596 | 6/1993 | Indig et al. | 204/435 |
| 5,465,281 | 11/1995 | Andresen et al. | 376/305 |
| 5,571,394 | 11/1996 | Hettiarachchi et al. | 204/400 |

OTHER PUBLICATIONS

"Electrochemical Sensors for Application to Boiling Water Reactors," ME Indig, Citations from Energy Science and Technology, (DOE): EDB ISS 94–13,94:08747 94001033757, pp. 4224–4236.

*Primary Examiner*—Charles T. Jordan
*Assistant Examiner*—M. J. Lattig
*Attorney, Agent, or Firm*—Noreen C. Johnson; Douglas E. Stoner

[57] ABSTRACT

An electrochemical corrosion potential sensor is fabricated by initially joining an electrical conductor to a sensor tip. An electrical cable is joined to the tip conductor. Ceramic powder is fused under heat around the tip conductor to form an integral annular electrically insulating band therearound to insulate the tip from the cable. The band may be formed by plasma spraying, or it may be molded and sintered to seal it to the tip and conductor without brazing. In a preferred embodiment, the band is formed of yttria-stabilized-zirconia or magnesia-stabilized-zirconia.

20 Claims, 2 Drawing Sheets

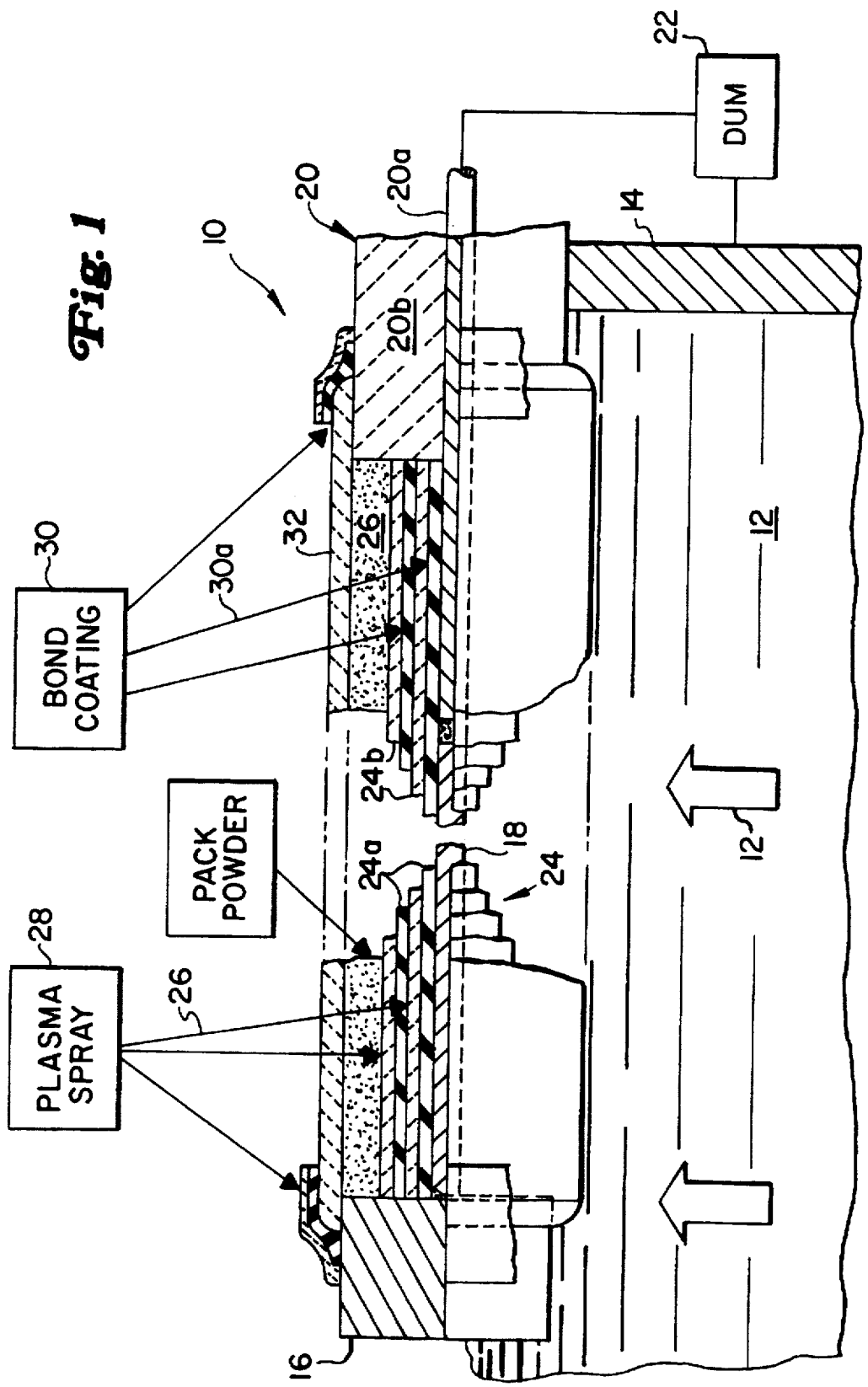

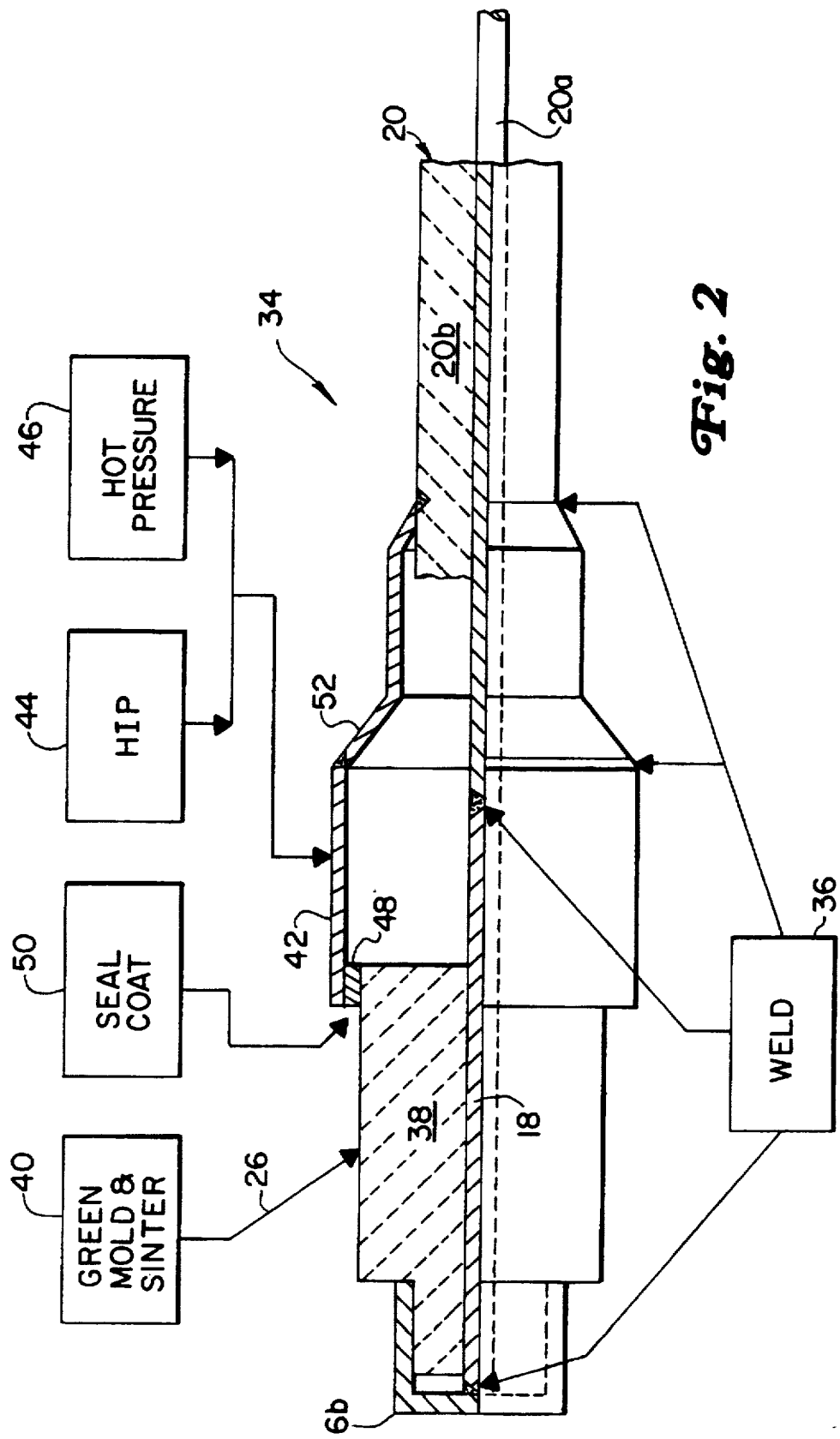

BRAZELESS ELECTROCHEMICAL CORROSION POTENTIAL SENSOR

BACKGROUND OF THE INVENTION

The present invention relates generally to nuclear reactors, and, more specifically, to electrochemical corrosion potential sensors.

A nuclear power plant includes a nuclear reactor for heating water to generate steam which is routed to a steam turbine which extracts energy therefrom for powering an electrical generator to produce electrical power. The nuclear reactor is typically in the form of a boiling water reactor having suitable nuclear fuel disposed in a reactor pressure vessel in which water is heated.

The water and steam are carried through various components and piping which are typically formed of stainless steel, with other materials such as alloy 182 weld metal and alloy 600 being used for various components directly inside the reactor pressure vessel.

It has been found that these materials tend to undergo intergranular stress corrosion cracking depending on the chemistry of the material, degree of sensitization, the presence of tensile stress, and the chemistry of the reactor water. By controlling any one or more of these critical factors, it is possible to control the propensity of a material to undergo intergranular stress corrosion cracking.

However, it is known that intergranular stress corrosion cracking may be controlled or mitigated by controlling a single critical parameter called the electrochemical corrosion potential of the material of interest. Thus, considerable efforts have been made in the past decade to measure the electrochemical corrosion potential of the materials of interest during the power operation of the reactor. This, however, is not a trivial task because the electrochemical corrosion potential of the material varies depending on the location of the material in the reactor circuit.

For example, a material in the reactor core region is likely to be more susceptible to irradiation assisted stress corrosion cracking than the same material exposed to an out-of-core region. This is because the material in the core region is exposed to the highly oxidizing species generated by the radiolysis of water by both gamma and neutron radiation under normal water chemistry conditions, in addition to the effect of direct radiation assisted stress corrosion cracking. The oxidizing species increases the electrochemical corrosion potential of the material which in turn increases its propensity to undergo intergranular stress corrosion cracking or irradiation assisted stress corrosion cracking.

Thus, a suppression of the oxidizing species is desirable in controlling intergranular stress corrosion cracking. An effective method of suppressing the oxidizing species coming into contact with the material is to inject hydrogen into the reactor water via the feedwater system so that recombination of the oxidants with hydrogen occurs within the reactor circuit. This results in an overall reduction in the oxidant concentration present in the reactor which in turn mitigates intergranular stress corrosion cracking of the materials, if the oxidant concentration is suppressed to very low levels.

This method is called hydrogen water chemistry and is widely practiced for mitigating intergranular stress corrosion cracking of materials in boiling water reactors. When hydrogen water chemistry is practiced in a boiling water reactor, the electrochemical corrosion potential of the stainless steel material decreases from a positive value generally in the range of 0.050 to 0.200 V(SHE) under normal water chemistry to a value less than -0.230 V (SHE), where SHE stands for the Standard Hydrogen Electrode potential. There is considerable evidence that when the electrochemical corrosion potential is below this negative value, intergranular stress corrosion cracking of stainless steel can be mitigated and the intergranular stress corrosion cracking initiation can be prevented.

Considerable efforts have been made in the past decade to develop reliable electrochemical corrosion potential sensors to be used as reference electrodes which can be used to determine the electrochemical corrosion potential of operating surfaces of components. These sensors have been used in more than a dozen boiling water reactors worldwide, with a high degree of success, which has enabled the determination of the minimum feedwater hydrogen injection rate required to achieve electrochemical corrosion potentials of reactor internal surfaces and piping below the desired negative value.

However, the drawback of these sensors is that they have a limited lifetime in that some have failed after only three months of use while a few have shown evidence of operation for approximately six to nine months.

Recent experience with two boiling water reactors in the United States has shown that the two major modes of failure have been the cracking and corrosive attack in the ceramic-to-metal braze used at the sensing tip, and the dissolution of the sapphire insulating ceramic material used to electrically isolate the sensing tip from the metal conductor cable for platinum and stainless steel type sensors.

The electrochemical corrosion potential sensors may be mounted either directly in the reactor core region for directly monitoring electrochemical corrosion potential of in-core surfaces, or may be mounted outside the reactor core to monitor out-of-core surfaces. However, the typical electrochemical corrosion potential sensor nevertheless experiences a severe operating environment in view of the temperature of the water well exceeding 88° C.; relatively high flowrates of the water up to and exceeding several m/s; and the high nuclear radiation in the core region. This complicates the design of the sensor since suitable materials are required for this hostile environment, and must be suitably configured for providing a watertight assembly for a useful life.

As indicated above, experience with the typical platinum electrochemical corrosion potential sensor has uncovered shortcomings that lead to premature failure before expiration of a typical fuel cycle.

Accordingly, it is desired to improve the design of electrochemical corrosion potential sensors for improving its useful life.

SUMMARY OF THE INVENTION

An electrochemical corrosion potential sensor is fabricated by initially joining an electrical conductor to a sensor tip. An electrical cable is joined to the tip conductor. Ceramic powder is fused under heat around the tip conductor to form an integral annular electrically insulating band therearound to insulate the tip from the cable. The insulating band may be formed by plasma spraying, or it may be molded and sintered to seal it to the tip and conductor without brazing. In the preferred embodiment, the band is formed of a chemically-stabilized-zirconia, such as yttria-stabilized-zirconia or magnesia-stabilized-zirconia. The invention, in accordance with preferred and exemplary embodiments, together with further objects and advantages thereof, is more particularly described in the following detailed description taken in conjunction with the accompanying drawings.

BRIEF DESCRIPTION OF THE DRAWINGS

FIG. 1 is a schematic representation of an exemplary electrochemical corrosion potential sensor and method of fabrication for use in a nuclear reactor.

FIG. 2 is a schematic representation of an electrochemical corrosion potential sensor and method of fabrication in accordance with an alternate embodiment of the present invention.

DETAILED DESCRIPTION OF THE INVENTION

In accordance with the present invention, improved methods of fabricating electrochemical corrosion potential sensors without using ceramic-to-metal braze, and without using sapphire as the ceramic insulator material are disclosed. Since the two modes of failure identified from field experience are eliminated, the life of the sensor is improved.

Illustrated schematically in FIG. 1 is an exemplary sensor 10 for measuring electrochemical corrosion potential in circulating water 12 in a vessel of a boiling water nuclear reactor 14 shown in relevant part in FIG. 1. The sensor 10 includes a sensor tip 16 which may have any suitable form such as a disk, or hollow or solid cylinder, and is formed of a suitable noble metal such as platinum or stainless steel. The sensor tip 16 is suitably electrically joined, by spot welding for example, to an electrical tip conductor 18 such as a platinum rod.

A mineral oxide insulating electrical cable 20 is suitably electrically joined to the tip conductor 18, and in turn is joined to a suitable device or digital voltmeter (DVM) 22 for measuring electrochemical corrosion potential of the reactor surface 14. The cable 20 may have any conventional configuration such as a central conductor or wire 20a having an end suitably spot welded to the corresponding end of the tip conductor 18. The cable conductor 20a is surrounded by a conventional electrically insulating sheath 20b, which may be a suitable mineral oxide ceramic.

A specifically fabricated and configured annular electrically insulating ceramic band 24 is bonded in accordance with one embodiment of the present invention to the tip 16 and its conductor 18 without ceramic-to-metal brazes. The band 24 provides complete electrical insulation of the entire length of the tip conductor 18 to its connection with the cable 20 and forms a hermetic, or water tight seal isolating this part of the sensor from the high temperature water environment of the reactor 14, as well as from other metal components in the system. The ceramic band 24 is formed of a suitable material other than sapphire for eliminating the known dissolution failure mode thereof. In a preferred embodiment, the insulating band 24 is formed of yttria-stabilized-zirconia or magnesia-stabilized-zirconia which have durability in the hostile nuclear reactor environment subject to high radiation, high water temperature, and high water flowrate up to about 1 m/s, and higher.

As shown in FIG. 1, the sensor 10 is fabricated by initially joining the tip conductor 18 coaxially to the center of the sensor tip 16, by spot welding for example. The electrical cable 20 is suitably joined to the tip conductor 18 by spot welding together the corresponding ends of the tip conductor 18 and the cable conductor 20a.

The insulating band 24 illustrated in FIG. 1 is formed by fusing under heat a ceramic powder 26 around the tip conductor 18, and a suitable portion of the cable conductor 20a to form the annular band 24 fixedly or integrally joined therearound to electrically insulate the tip 16 from the cable 20, across its sheath 20b radially outwardly from the cable conductor 20a. In a preferred embodiment, the fusing is accomplished by using a conventional plasma spraying apparatus 28 for integrally bonding and sealing the powder 26 to the tip 16 and its conductor 18 to form a hermetic seal with electrically insulating properties. The yttria-stabilized-zirconia band 24 is used instead of a solid sapphire insulator, and therefore eliminates the failure modes of sapphire dissolution and degradation of ceramic-to-metal braze joints associated with the sapphire insulator.

The ceramic powder 26 may be bonded to the tip conductor 18 in any manner. In the preferred embodiment illustrated in FIG. 1, a suitably rough bond coating 24a is firstly applied around the tip and cable conductors 18, by any bond coating apparatus 30, which may also be a plasma sprayer. The bond coating 24a may be applied in any suitable thickness, for example 5–10 mils (0.127–0.254 mm) of a suitable material such as a M-Chromium-Alumina-Yttrium alloy (MCrAlY alloy) where M=NiCoFe or Ni+Co. The bond coating 24a provides a suitably rough bond coat surface which may be effected by using a suitably coarse mesh bond coat powder 30a. The ceramic powder 26 is then plasma sprayed atop the bond coating 24a to form a corresponding ceramic coating 24b as a top coat. The ceramic coating may have any suitable thickness such as about 20–40 mils (0.508–1.02 mm) of ceramic coating.

Preferably, a plurality of the bond and ceramic coatings 24a,b are successively applied atop the tip and cable conductors 18, 20a to effect redundant layers of electrical insulation and hermetic sealing.

An additional level of redundancy may be obtained by using a preformed ceramic tube or sleeve 32 slidably positioned around the band 24. The sleeve 32 is formed of a suitable material such as yttria-stabilized-zirconia having a suitable internal diameter slightly larger than the outer diameter of the tip 16 and cable 20 so that it may be simply slid into position axially thereover. The sleeve 32 has a suitable length to completely cover the band 24 and preferably overlaps respective portions of the tip 16 and cable 20.

An additional amount of the ceramic powder 26 may be suitably packed or filled between the inner diameter of the sleeve 32 and the outer diameter of the band 24, as the sleeve 32 is assembled, for removing any voids therebetween to provide additional insulation and sealing.

The opposite ends of the sleeve 32 may then be suitably sealed to the corresponding overlapped portions of the sensor tip 16 and cable 20. This may be accomplished by plasma spraying additional amounts of the ceramic powder 26 over the sleeve ends, which is preferably accomplished by first applying corresponding bond coatings thereto using the apparatus 28 and 30.

The band 24 when fabricated will have an outer exposed surface or perimeter formed of the fused ceramic powder, which is preferably yttria-stabilized-zirconia. The band 24 provides suitable electrical insulation and hermetic sealing for use in the hostile environment of the reactor 14. As indicated above, however, the band 24 is preferably formed in layers of the ceramic coating 24b for providing redundancy.

Further redundancy is provided by the packing powder 26, also preferably yttria-stabilized-zirconia, and the finally enclosing sleeve 32, also preferably yttria-stabilized-zirconia. The ends of the sleeve 32 are plasma spray sealed to the tip 16 and the cable 20, again preferably using yttria-stabilized-zirconia.

In this way, multiple levels are provided for providing electrical insulation between the sensor tip 16 and the cable 20 while hermetically sealing the tip and cable conductors 18, 20a. The exposed sensor tip 16 is therefore effective for measuring electrochemical corrosion potential of the surface of the reactor 14, and is suitably electrically insulated from the remainder of the cable 20 and any adjoining metal components of the reactor 14. No ceramic-to-metal brazing or sapphire as an insulator are required. The resulting sensor is effective in the hostile nuclear environment, but is newly fabricated for improving its useful life by eliminating known failure modes found in sapphire electrochemical corrosion potential sensors.

Illustrated schematically in FIG. 2 is an alternate embodiment of a electrochemical corrosion potential sensor 34. In this embodiment, the sensor tip 16b is in the form of a hollow cap or cup preferably made of platinum or stainless steel. The tip conductor 18 is suitably spot welded to the center of the tip 16b by a welding apparatus 36.

In this embodiment, a one-piece electrically insulating and hermetically sealing annular band 38 is fusion bonded directly to the tip conductor 18 and inside the tip 16b. This may be accomplished by using a Green ceramic cylindrical mold 40 followed by sintering at an elevated temperature, such as about 1450° C. The ceramic powder 26, which is preferably yttria-stabilized-zirconia, is packed in the mold and sintered for fusing the powder and bonding it in a one-piece construction to the tip 16b and conductor 18.

A cylindrical metal sleeve 42 is suitably disposed around the proximal end of the insulating band 38, and is spaced axially apart from the sensor tip 16b. The sleeve 42 may be made of a suitable metal such as Kovar, which is an iron-nickel-cobalt alloy. The sleeve 42 may be also formed of Alloy 42 or Invar, an iron-nickel alloy without cobalt.

The sleeve 42 is preferably fused to the insulating band 38 using hot isostatic pressuring (HIP) effected by suitable apparatus 44 therefor. Typical hot isostatic pressuring conditions for this purpose include temperatures in the range of about 1,000 to 1,200° C. and pressure of about 200 Mpa in an inert gas environment, such as argon.

Alternatively, the sleeve 42 may be fused to the band 38 using a hot pressure process with corresponding apparatus 46 which may be performed at about 1,000° C. and a pressure of about 300 psi (2.1 MPa).

In both of these processes, either the outer diameter of the band 38 or the inner diameter of the sleeve 42 is preferably coated with a seal coating 48, which may be a layer of platinum applied using a coating apparatus 50 for effecting electroplating or sputtering thereof. The platinum seal coating 48 under the hot isostatic pressuring or hot pressure processes forms a suitable hermetic seal between the metal sleeve 42 and the ceramic band 38. In this way, a metal sleeve is suitably secured to the ceramic band 38 for providing a rigid support. The resulting metal-to-ceramic joint is not formed by brazing which would be subject to cracking or corrosion during operation.

The metal sleeve 42 may then be suitably welded using the welder 36 specifically configured therefor, to a tubular transition piece 52, which may be formed of stainless steel for the nuclear reactor environment. The transition piece 52 is in turn suitably welded or brazed to the cable 20. Since the central conductor 20a of the cable 20 is suitably spot welded to the end of the tip conductor 18, welding of the transition piece 52 to the metal sleeve 42 completes the fabrication of the sensor 34. The sensor 34 is therefore fabricated using the ceramic insulating band 38 instead of sapphire, and without ceramic-to-metal brazes, thereby eliminating the corresponding failure modes therefrom.

In both of the exemplary electrochemical corrosion potential sensors 10, 34 disclosed above, the basic elements of the sensor including the platinum tip 16, 16b and connecting cable 20 are utilized. However, suitable electrical insulation and hermetic sealing are provided using different embodiments of the fused ceramic material forming the respective bands 24, 38. Electrical insulation and hermetic sealing are provided without using sapphire or ceramic-to-metal brazes having known failure modes in the hostile environment of the nuclear reactor 14.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

What is claimed is

1. A method of brazeless bonding of dissimilar materials to fabricate a sensor for measuring electrochemical corrosion potential in a nuclear reactor comprising:
   joining an electrical tip conductor to a sensor tip;
   joining an electrical cable to said tip conductor; and
   fusing under heat a ceramic powder around said tip conductor to form an integral annular electrically insulating band therearound.

2. A method according to claim 1 wherein said band is also bonded to said tip conductor to form a hermetic seal.

3. A method according to claim 2 wherein said band includes an outer exposed surface formed of yttria-stabilized-zirconia or magnesia-stabilized-zirconia.

4. A method according to claim 3 wherein said fusing step comprises plasma spraying said powder over said tip conductor.

5. A method according to claim 4 wherein said fusing step further comprises:
   firstly applying a bond coating to said tip conductor; and
   secondly plasma spraying said ceramic powder over said bond coating to form a ceramic coating thereon.

6. A method according to claim 5 further comprising applying successively a plurality of said bond and ceramic coatings atop said tip conductor to effect redundant layers of electrical insulation and sealing.

7. A method according to claim 6 further comprising:
   positioning a pre-formed ceramic sleeve around said band; and
   sealing said sleeve at opposite ends thereof to said tip and said cable.

8. A method according to claim 7 further comprising packing a ceramic powder between said sleeve and said band to remove voids therebetween, prior to sealing said sleeve to said cable.

9. A method according to claim 8 wherein both said sleeve and packing powder are yttria-stabilized-zirconia.

10. A method according to claim 9 wherein said sealing step comprises plasma spraying additional amounts of said ceramic powder over said sleeve ends at said tip and said cable.

11. A method according to claim 3 wherein said fusing step comprises molding and sintering said ceramic powder over said tip conductor to form a one-piece insulating band bonded to said sensor tip.

12. A method according to claim 11 further comprising fusing a metal sleeve around one end of said band spaced apart from said sensor tip.

13. A method according to claim 12 wherein said sleeve fusing step comprises hot isostatic pressing of said sleeve to said band.

14. A method according to claim 12 wherein said sleeve fusing step comprises hot pressure bonding of said sleeve to said band.

15. A method according to claim 12 further comprising:
   welding said sleeve to a metal transition piece; and
   welding said transition piece to said cable, with said cable having a central conductor spot welded to said tip conductor.

16. A sensor for measuring electrochemical corrosion potential in a nuclear reactor comprising:
   a sensor tip electrically joined to a conductor;
   electrical cable electrically joined to said tip conductor; and
   an annular electrical insulating ceramic band bonded to said tip and tip conductor without ceramic-to-metal brazes.

17. A sensor according to claim 16 wherein said band comprises a plurality of layers of fused ceramic powder.

18. A sensor according to claim 16 wherein said band comprises a plurality of alternating layers of fused ceramic powder atop corresponding bond coatings.

19. A sensor according to claim 16 further comprising a ceramic sleeve surrounding said band, and sealingly joined to said sensor tip and cable, and said band and sleeve comprise yttriastabilized-zirconia or magnesia-stabilized-zirconia.

20. A sensor according to claim 16 wherein said band comprises fused ceramic powder bonded in one-piece to said tip and conductor.

* * * * *